US005730727A

United States Patent [19]
Russo

[11] Patent Number: 5,730,727
[45] Date of Patent: Mar. 24, 1998

[54] THUMB CONFORMABLE SUCTION CONTROL REGULATOR

[76] Inventor: Ronald D. Russo, 8 Candleberry Rd., Barrington, R.I. 02806

[21] Appl. No.: 601,167

[22] Filed: Feb. 14, 1996

Related U.S. Application Data

[60] Provisional application No. 60/000,130, Jun. 12, 1995.
[51] Int. Cl.[6] .................................................. A61N 1/00
[52] U.S. Cl. ......................... 604/118; 604/119; 137/517
[58] Field of Search ................................ 604/118, 119; 251/342, 354; 137/517, 859

[56] References Cited

U.S. PATENT DOCUMENTS

| Re. 32,553 | 12/1987 | Bennett | 137/859 |
|---|---|---|---|
| 2,690,734 | 10/1954 | Heckendorf | 251/342 |
| 3,174,694 | 3/1965 | Kitabayashi | 251/342 |
| 3,595,234 | 7/1971 | Jackson | 604/119 |
| 3,595,445 | 7/1971 | Buford | 251/342 |
| 3,958,566 | 5/1976 | Furihata | 604/119 |
| 4,149,650 | 4/1979 | Whelchel | 251/354 |
| 4,287,889 | 9/1981 | Stupar | 604/119 |
| 4,356,823 | 11/1982 | Jackson | 604/119 |
| 4,534,542 | 8/1985 | Russo | 604/119 |

*Primary Examiner*—Sam Rimell
*Assistant Examiner*—Luke J. Yeh
*Attorney, Agent, or Firm*—Robert J. Doherty

[57] ABSTRACT

A suction control regulator for use with a medical suction catheter wherein the regulator includes a rigid molded body attached to a flexible suction catheter at its front and connectable to a source of suction at its rear. An intermediate portion is located between the front and rear portions to act as a means for regulating suction. The intermediate portion includes an outwardly extending stem with an inner passage, the stem terminating in an oval-shaped contoured flange which generally conforms in shape to the contour of the user's thumb. A resilient boot is mounted on the stem and the boot includes a flat diaphragm top suspended and free floating above the stem flange when positioned in a normally open to atmosphere non-suction applied position. The diaphragm top is depressible downward by the thumb to conform to the shape of the flange to seal off the inner passage to close the passage to atmosphere to a suction applied position. The diaphragm protects the user's thumb from contact with aspirated secretions during operation of the device.

33 Claims, 10 Drawing Sheets

THUMB CONFORMABLE SUCTION CONTROL REGULATOR

This application claims the benefit of U.S. Provisional application Ser. No. 60/000,130 filed Jun. 12, 1995.

BACKGROUND AND SUMMARY OF THE INVENTION

Suction control regulators for use with medical devices especially suction catheters for removing accumulated secretions in a patient's trachea are well known in the prior art. Single use disposable suction catheters are packaged sterile and are typically low cost devices that are used once and then discarded. Halligan in U.S. Pat. No. 3,319,628 was one of the first inventors to disclose a simple plastic one-piece molded suction control valve for use with suction catheters. The Halligan U.S. Pat. No. 3,319,628 describes a plastic catheter attached to a valve consisting of a central continuous non-obstructed lumen attachable at its proximal end to a source of suction. Midway to the central lumen is a side stem also with a passage which terminates in a circular flange open to atmosphere. Suction is controlled by simply closing off the flange with the user's thumb. The Halligan valve was commercialized in 1966 and since that date hundreds of millions of the Halligan suction control catheters have been sold. Coyne in U.S. Pat. No. 3,937,220 uses the same Halligan valve but adds a pliable sleeve to protect the catheter from touch contamination. Russo in U.S. Pat. No. 4,534,542 also uses the same Halligan valve structure but adds a circular raised button in an attempt to protect the user's thumb from contacting aspirated secretions.

Other patents of interest are U.S. Pat. No. 3,595,234 to Jackson who in 1969 was the first to add an elastic band to cover the suction control opening in another attempt to prevent contamination. This band was a tight fitting band which stretched around the entire body of the valve. The 1981 U.S. Pat. No. 4,287,889 to Stupar shows a tubular oval-shaped band which loosely surrounds the valve body. Neither the Jackson nor the Stupar devices were ever commercialized because they suffered from performance difficulties. The band of Jackson has a tendency to get sucked into the control opening and would thus get stuck in the suction applied position. The elastic band was simply stretched over the valve body with no positive means for holding it in place. The user's thumb could easily slide off the band making the device inoperable. Stupar makes note of all the problems with Jackson and tries to secure his tubular band with an L-shaped arm yet requires that in application the band "can be secured to the body by chemical or mechanical means". How this securing means is to be done is never described. Stupar still has a rubber band which still has all the problems of the Jackson device.

Russo in the 1985 U.S. Pat. No. 4,534,542 was the first to have a molded cap which snapped securely into place but is limited to a generally circular opening and one in which the vent openings although not positioned in the contact button are disposed in the cap top and would be in line with the user's thumb in use thus raising a question of possible contact with contaminants. This device, however, was commercialized in 1986 and is still being marketed.

Catheters that use narrow width oval-shaped suction control valves are now much preferred over the round or circular shape of Russo's U.S. Pat. No. 4,534,542. They are termed slim-line in that they are less bulky and can be packaged more easily using automatic sterile packaging machines. By using less packaging materials, total product cost is reduced.

All of the above devices are generally termed normally open to atmosphere valve structures, and they function about the same as the original Halligan valve. It is important to note that all the above normally open to atmosphere valves use a circular flange, and the use and function of the valves are very adequately described in all these prior art inventions. The device of Russo in U.S. Pat. No. 4,534,542 has also been commercialized but the circular valve cap adds considerable bulk to the profile of the device such that larger and more costly packaging is required.

The instant invention uses the classical normally open to atmosphere one-piece injection molded valve body yet markedly improves it to provide a flatter profile for ease of packaging and lower cost and provides a unique contoured booted cover to conform to the user's thumb to easily regulate applied suction and give the user infection control protection from aspirated secretions. The instant invention uses a body which in the preferred embodiment comprises a conventional T-tube structure but instead of a circular side stem and flange configuration, it preferably has a flat sided oval-shaped passage with a varied edged slightly concave contoured flange which readily conforms to the user's thumb. A unique one-piece molded rubberized boot cover is mounted over the contoured flange and stem to provide a protective cover for both regulating suction and protecting the user from contacting potentially infectious secretions during the operation of the regulator. The boot cover follows the varied contours of the body to provide a low profile and has a unique means for mounting on the body stem and flange. The boot cover has a full side skirt which runs around the periphery of the side stem and bottoms out on the central portion of the body. This mounting means permits the boot cover to be configured on any type of varied contoured stem or flange. The cover is thus permitted to slightly free float around and over the side-stem and contoured flange such that it fully surrounds and protects it. The cover has a stop resilient diaphragm preferably integrally therewith and molded which is suspended above the body flange and oval stem outlet passage. While the outlet passage itself is preferably oval shape for better thumb confirmation, the lower part of the outlet passage need not be so configured, that is, there is no operational advantage to make the passage oval. Also, although not as desirable, the opening could also be circular as could the body stem flange itself. Outboard of the diaphragm are two vent slots which permit suction to be normally vented open to atmosphere to prevent suction from being applied to the catheter.

Thumb depression of the diaphragm will permit the diaphragm to flex and conform to the shape of the thumb. Continued depression permits the diaphragm to conform to the contoured slightly concave shape of the flange thus sealing off the irregularly shaped oval outlet passage in the flange to cut off vented suction and to permit suction to then be applied to the catheter. The thumb can be moved slightly up or down or in a slight back and forth sliding motion of the thumb to provide a very sensitive means for regulating the degree of suction applied. Releasing the thumb fully will return the device to its original normally open to atmosphere non-suction applied position. Since the diaphragm substantially covers the top of the flange and the outlet passage, it provides thumb protection against secretion contact such that the user does not need expensive sterile gloves to operate the regulator. Non-sterile inexpensive exam gloves can be used if desired.

Accordingly, it is seen that the instant invention provides a low profile and highly effective device for regulating the degree of suction applied in a medical catheter and can be easily designed to conform to any designed non-circular valve flange. Further, the regulator provides a very effective means for protecting the user from contacting aspirated secretions as well as reducing and controlling the spurting and aerosolization of potentially infectious bacteria or viruses into the environment.

It is therefore a primary objective of the invention to provide an effective suction control regulator in a low profile slim line configuration.

Another objective is to provide a suction control regulator which can be adapted to any configuration of thumb control action.

Another objective is to provide a suction control regulator which protects the user from contacting aspirated secretions during repeated activations of the regulator either in an on-off or intermittent suction applied mode.

Other objects and advantages of the invention and its variations shall become apparent from the description of the invention and the accompanying drawings.

DESCRIPTION OF THE DRAWINGS

In the drawings which illustrate the best mode presently contemplated for carrying out the present invention.

DETAILED DESCRIPTION OF THE INVENTION

Figure 1:
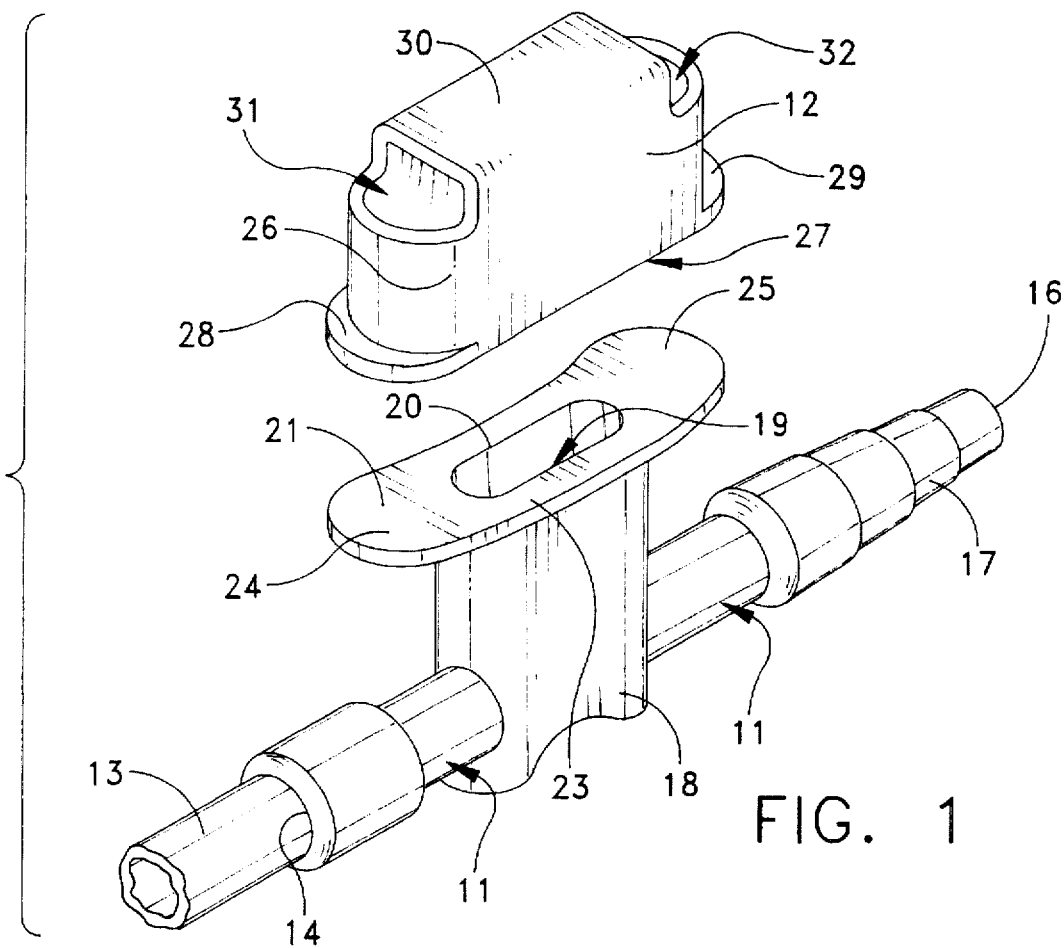
FIG. 1 is an exploded perspective view of the preferred embodiment showing the valve body and boot cover.
Figure 2:
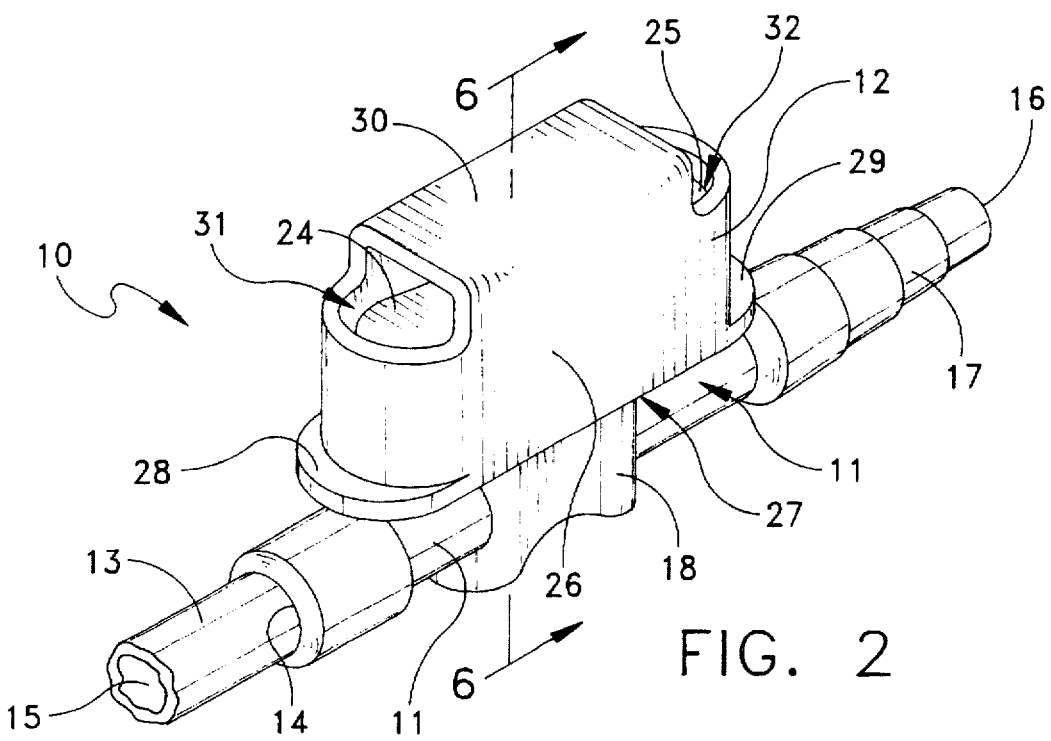
FIG. 2 is a perspective view of the boot cover installed on the valve body shown in FIG. 1.

Referring now to the drawings, the three main components of the preferred embodiment are illustrated in FIGS. 1 and 2. The suction control regulator 10 comprises a rigid injection molded body 11, a flexible boot cover 12 and an attached flexible suction catheter 13.

The body is typically molded in one piece in rigid PVC plastic to which the catheter 13 is usually solvent cemented into the body at its frontal inlet 14. The body 11 includes an unobstructed lumen 15 which at its front end forms a continuing passage through body 11 and exits at the rear or proximal end of the body through exit 16. Exit 16 in turn is formed through a connector portion such that standard suction tubing may be attached to the proximal end of the body and tapered barb fittings 17 are provided for such purpose. Midway to the central lumen is flat sided side stem 18 which has an interior oval-shaped inner passage 19 with a central axis which is in fluid communication with the central lumen 15. The passage 19 terminates in an oval-shaped outlet 20. A concave-shaped matching flange 21 flares outward from the outlet 20. The flange 21 has two narrow low profile side edges 22 and 23. Opposite these side edges is extended contoured tabs 24 and 25 forming a varied periphery. Boot cover 12 has a fully contoured skirt or side wall 26 which follows the varied contours of flange 21. The boot has a bottom ledge 27 which when mounted over the flange 21 rests firmly on the main body 15 at side ledges 28 and 29. The boot has a top diaphragm 30 with two side vent slots 31 and 32 positioned outboard of the top diaphragm 30.

Figure 3:
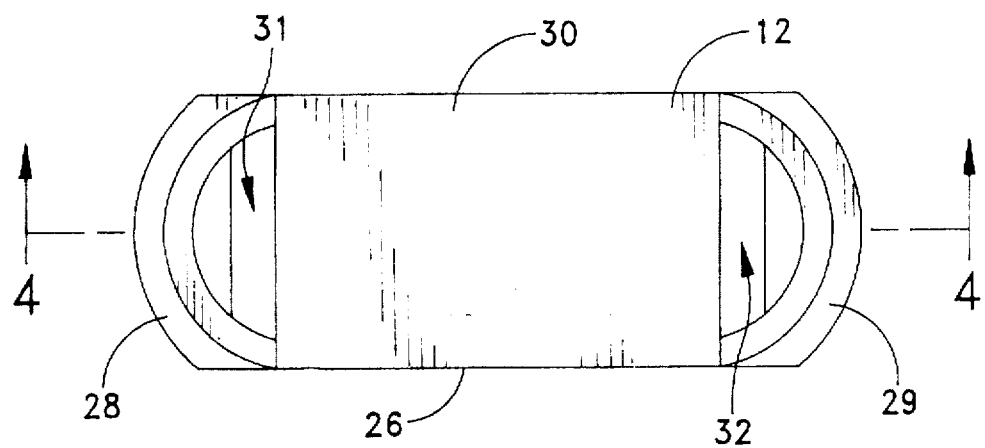
FIG. 3 is a top view of the boot cover showing the two vent slots outboard of the diaphragm.

FIG. 3 is a top view of boot cover 12.

Figure 3A:
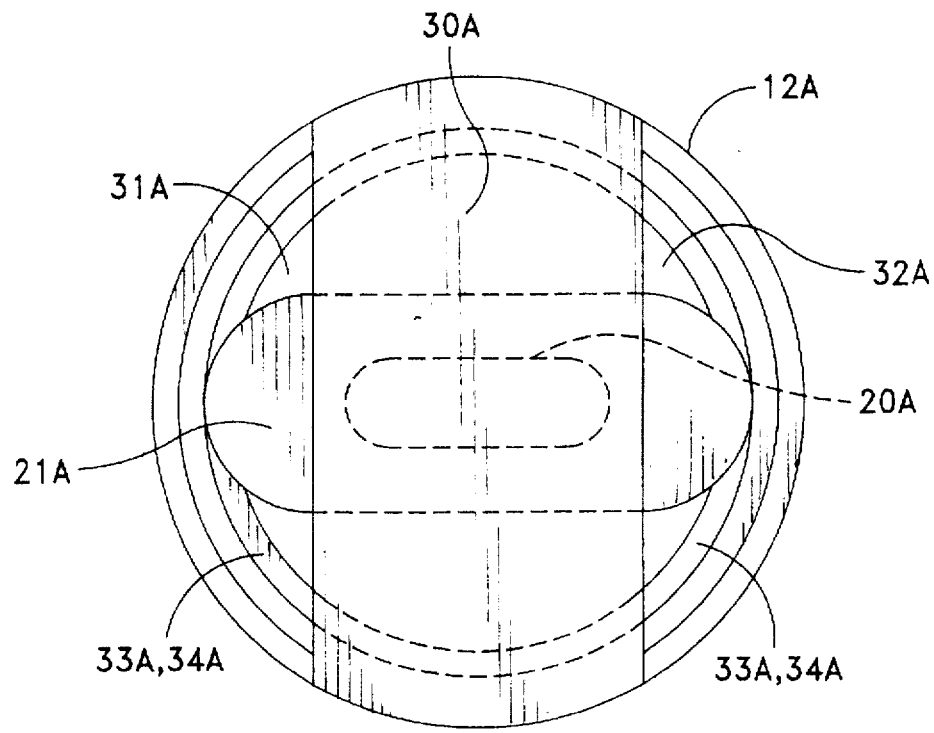
FIG. 3A is a top view of an alternate shaped boot cover shown installed upon the valve body of FIG. 2.
Figure 3B:
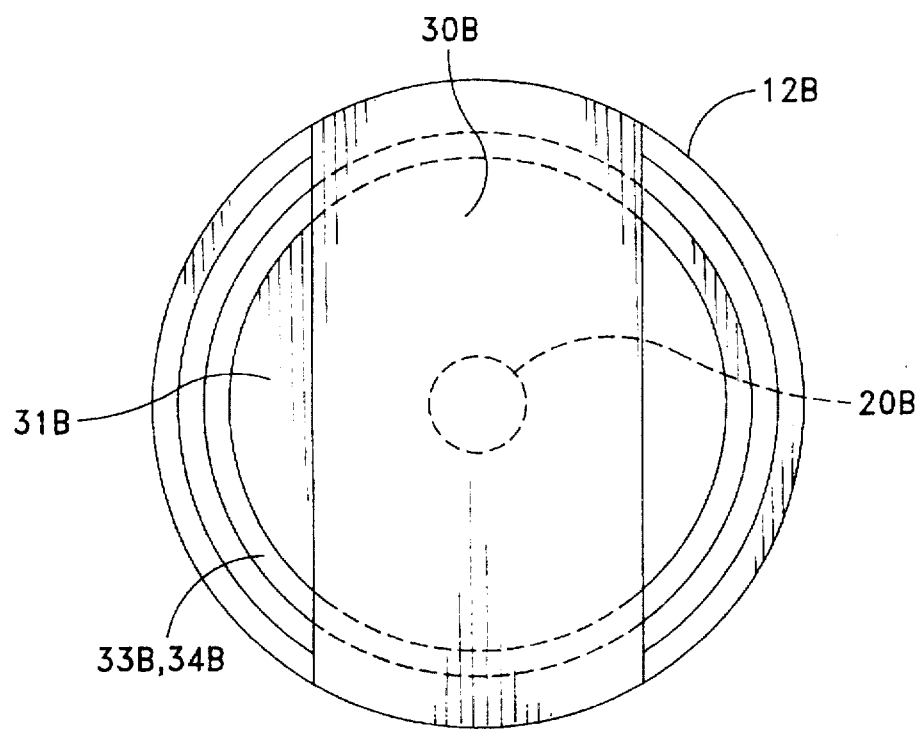
FIG. 3B is a top view of the alternate shaped boot cover shown in FIG. 3A but installed on an alternatively shaped valve body stem from that shown in FIGS. 1 and 2.

FIGS. 3A and 3B illustrate that, although the primary use of the invention is with the elongated oval side stem configuration presently commercially favored, the side stem 18A, 18B, the side stem flange 21A, 21B and the passage 19A, 19B, and the opening 20A, 20B could be respectively of oval or round configuration and that in such cases where the rounded form, although not preferred because of bulk and size considerations, is utilized, then the skirt 20A, 20B conforms to such configuration.

Figure 4:
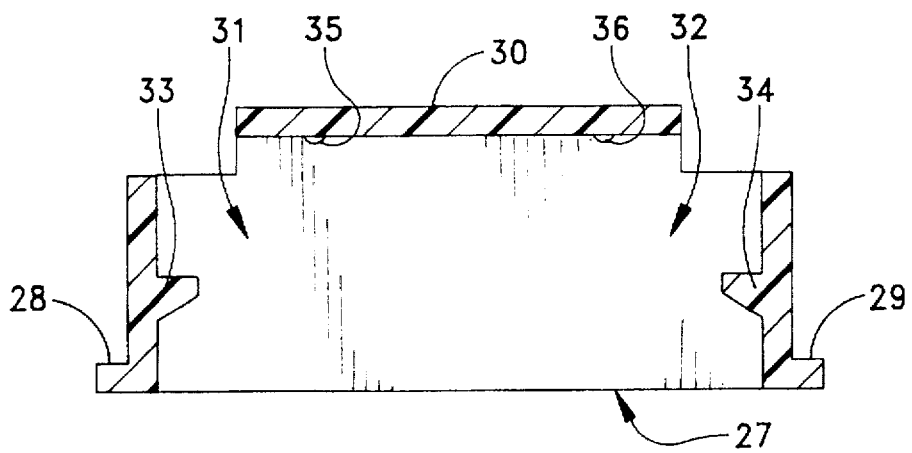
FIG. 4 is a cross-sectional view of the boot cover taken along line 4—4 in FIG. 3.

FIG. 4 is a cross-sectional view of the cover. Internal to the cover are under-lugs 33 and 34 which flex outward to permit the cover to be pressed down over tabs 24 and 25 on the flange 21 to capture the cover 12 onto the valve body 11.

On the underside of diaphragm 30 are molded in detent bumps 35 and 36 which act as vacuum breakers to prevent the top diaphragm from sticking into outlet 20 on flange 21 in case very high vacuum levels above 15 inches of mercury are applied to the catheter to rapidly clear the trachea of secretions during an emergency situation.

Figure 5:
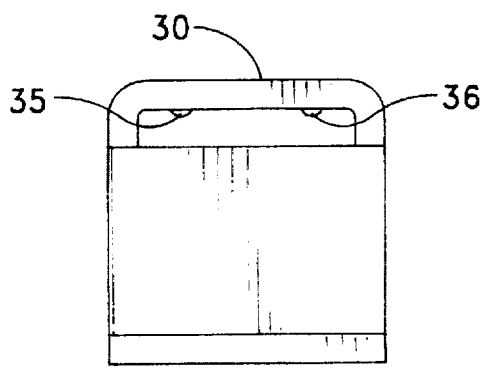
FIG. 5 is an end view of the boot cover shown in FIGS. 1-4.

FIG. 5 is a side view of the cover depicting the underside bumps 35 and 36.

Figure 6:
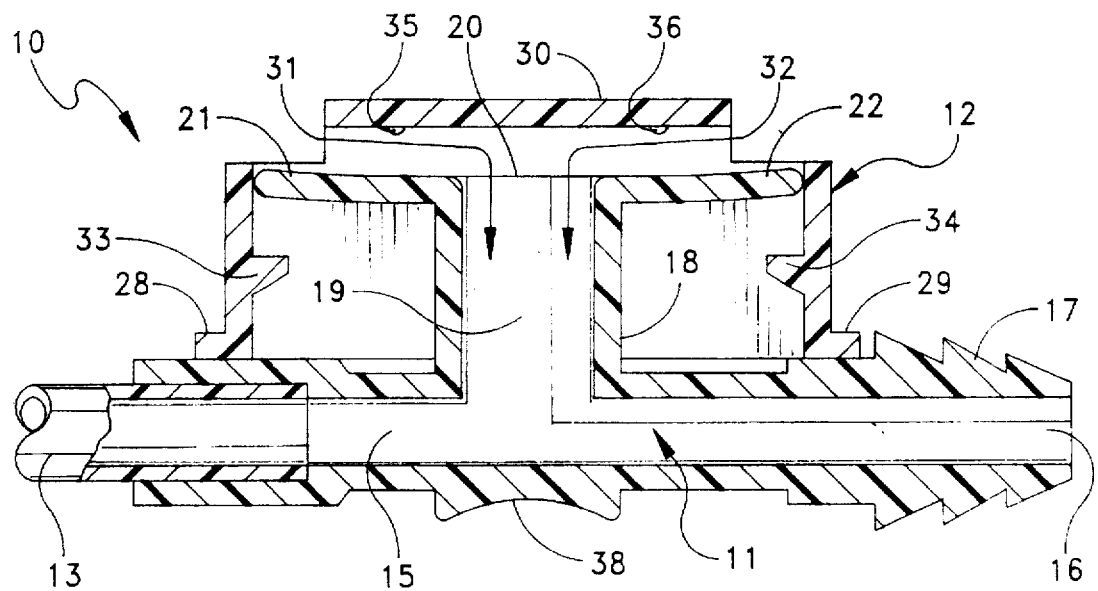
FIG. 6 is a cross-sectional view of the boot cover shown in FIGS. 1-5 installed on the valve body shown in FIGS. 1 and 2 in its normally non-suction applied open to atmosphere position taken along line 6—6 in FIG. 2.

FIG. 6 is a clear cross-sectional view of the regulator 10 with boot cover 12 fully mounted on valve body 11 with catheter 13 attached in its normally vented to atmosphere non-suction applied position.

When suction is applied to connector 17, suction enters outlet 16 and permits vented air to be sucked into the valve body 11 through vent slots 31 and 32 on boot cover 12. Suction, therefore, never gets applied directly to the catheter.

Figure 7:
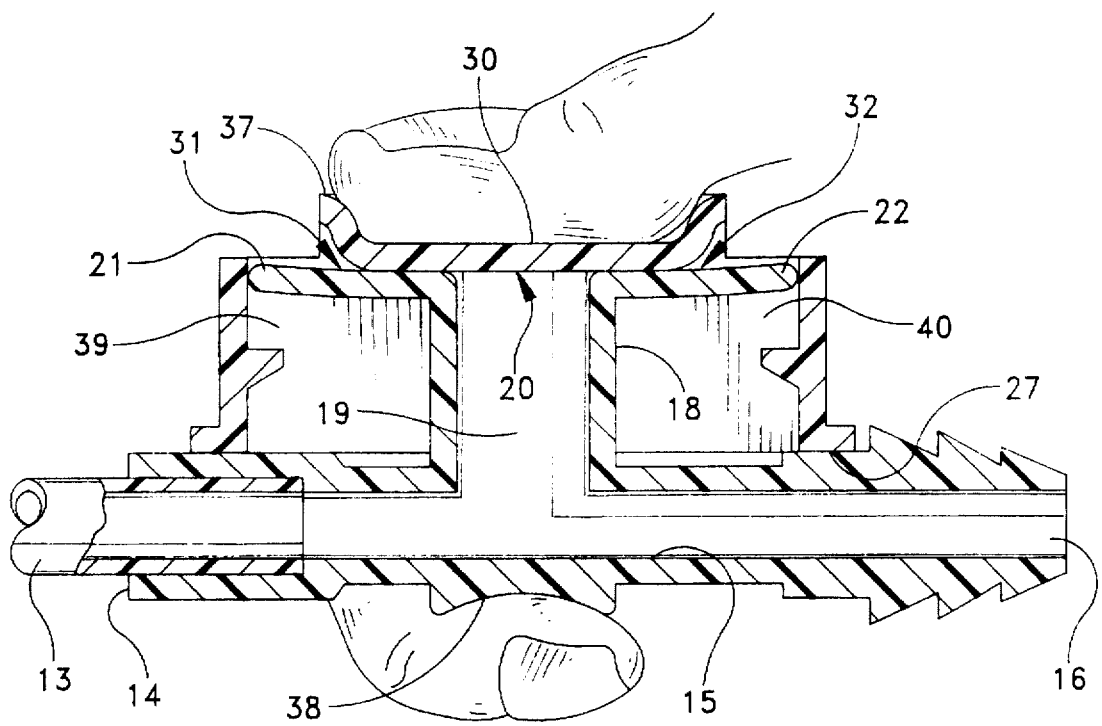
FIG. 7 is a similar view as shown in FIG. 6 but showing the boot cover in the closed suction applied position.

FIG. 7 shows the same cross-sectional view when the user's thumb depresses diaphragm 30 which conforms to the user's thumb.

Diaphragm 30 flexes downward to close off oval-shaped outlet 20 and inner passage 19 which means that all the suction can then be applied to the catheter since none of the suction is lost to atmosphere via outlet vent 20. A slight lifting of the tip of the thumb 37 is all that is required to permit some vented air to enter the outlet 20 to vary or regulate the suction applied.

The underside of valve body 11 can have a molded in finger rest 38 which helps in varying the suction from either on-off or to slight varying pressure to partially open the outlet 20 to vary, regulate or control the level of suction applied as desired.

As can be seen from FIG. 6 and FIG. 7, the boot cover is mounted over the side stem 18 by under-lugs 33 and 34 and seats directly on top of body 15 by ledge 27. As such, the cover becomes an enclosure boot that is retained from being pulled off by lugs 33 and 34 yet can free float slightly up and down through gaps 39 and 40. This permits the boot cover 12 to suspend the diaphragm 30 above flange 20 without having to directly engage flange 20 which means that the cover 12 can act independently of the flange 20. This independent support of the boot cover 12 permits it to enclose any shape stem or flange no matter how odd the contour, profile, or shape. For instance, the cover could easily enclose a flat topped oval flange or a slightly convex contoured flange.

It should also be pointed out that it is not necessary that the closure skirt or side wall 26 make air tight contact with the flange profile. Such, in essence, free floating of the closure boot at least with respect to the flange or stem enables accommodation of a wide range of stem and flange shapes such as those not only shown in FIGS. 3A, 3B but also in the various alternative embodiments that will hereinafter be referred to.

Figure 8:
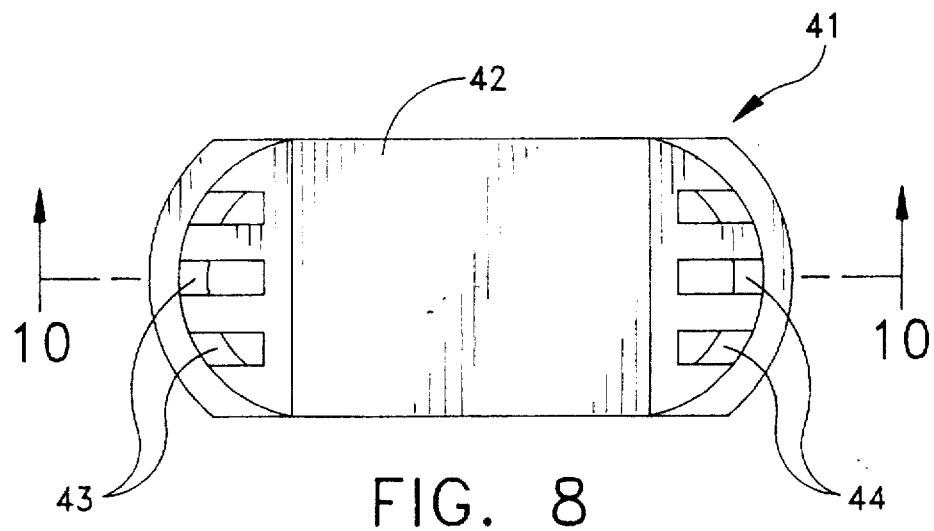
FIG. 8 is a top view of a first alternate embodiment of the valve cover.

FIG. 8 is a top view of a first alternate embodiment of the invention depicting boot cover 41 with top diaphragm 42 and multiple slotted side vents 43 and 44.

Figure 9:
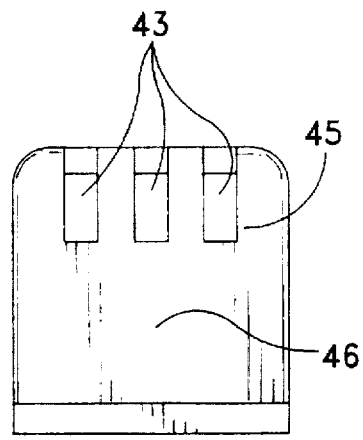
FIG. 9 is a side view of the valve cover of FIG. 8.

FIG. 9 is an end view showing multiple slots 44 terminating partially down side wall 46 at point 45.

It is important to note that the total area of all vented slots whether multiple or singular should at least add up to the total square area of the stem passage to prevent any internal suction build up within the valve body from being applied to the catheter lumen if the catheter and suction regulator valve is left connected to a suction line.

Figure 10:
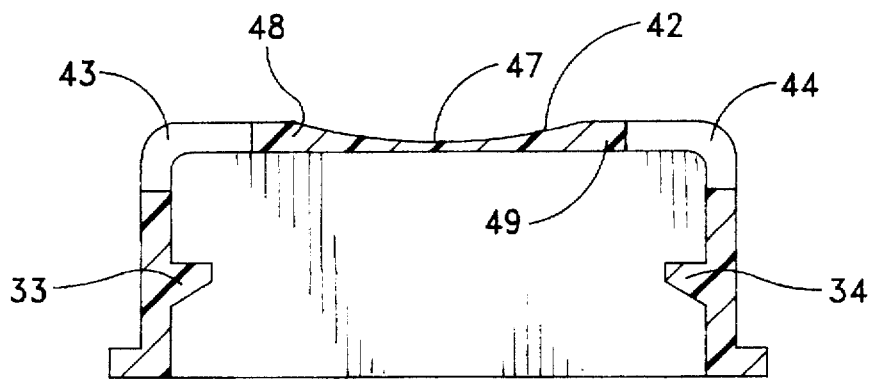
FIG. 10 is a cross-sectional view of the first alternate embodiment taken along line 10—10 of FIG. 8.

FIG. 10 is a cross-sectional view of the cover depicted in FIG. 9 and it depicts concave-shaped diaphragm 42 with a thin middle section 47 and thicker ends 48 and 49. This configuration gives a very sensitive touch to the diaphragm at its thinner middle section 47 with a high degree of instantaneous return action due to its thicker ends 48 and 49. Such centrally thinned top wall closure could also be utilized with the previously described embodiment if desired.

Figure 11:
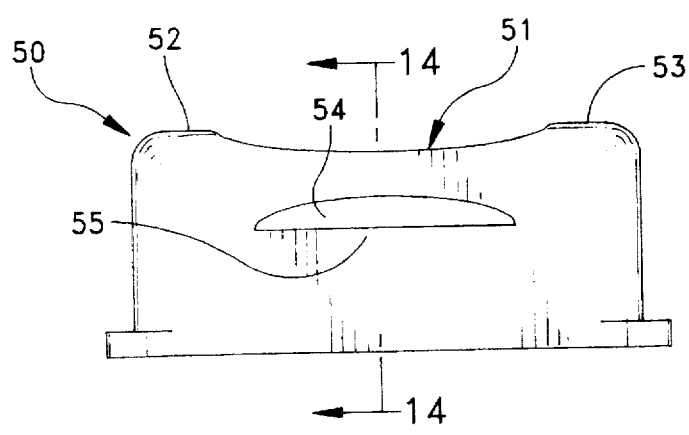
FIG. 11 is a side view of a second alternate embodiment showing a side vent slot in a normally open to atmosphere non-suction applied position.
Figure 12:
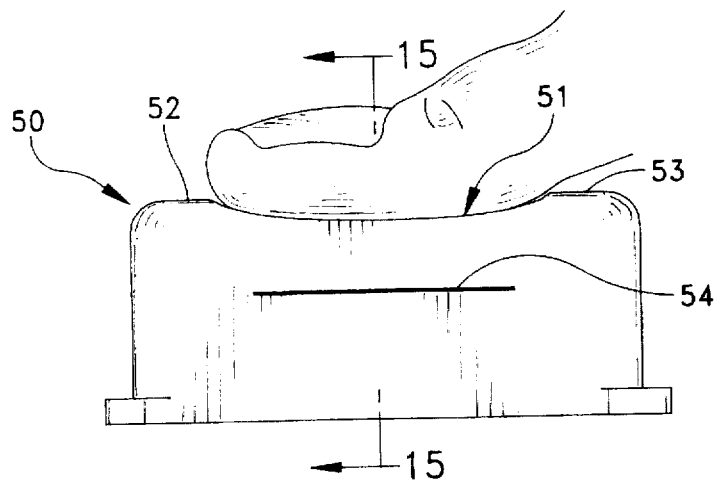
FIG. 12 also is a side view of the second alternate embodiment showing a thumb depressed side vent slot sealed closed to a suction applied position.

FIG. 11 depicts a side view of a second alternate cover 50 also having a concave middle section 51 with higher thicker end sections 52 and 53. An arched-shaped slot 54 on side wall 55 permits venting to atmosphere to occur in its normally non-depressed, non-suction applied position. When diaphragm 51 in FIG. 12 is depressed by thumb pressure, it compresses arched-shaped slot 54 to seal the internal passage stem to atmosphere to permit all the suction to then be applied to the catheter.

Figure 13:
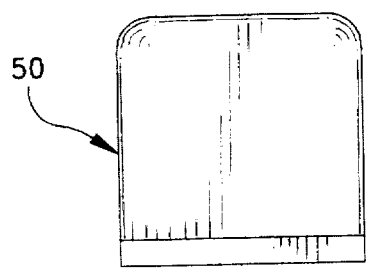
FIG. 13 is an end view of the second alternate embodiment.

FIG. 13 is an end view of second alternate cover 50 showing no end slots or slots in the top of the cover.

Figure 14:
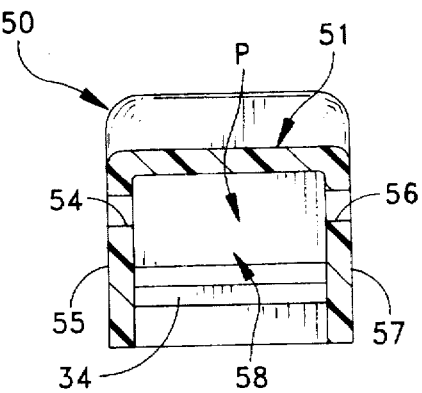
FIG. 14 is a cross-sectional view of the second alternate embodiment depicting the arched shaped slot in its normally open non-depressed non-suction applied state taken along line 14—14 of FIG. 11.

FIG. 14 is a cross-sectional view of second alternate cover 50 showing arched-shaped slot 54 in side wall 55 and another arched-shaped slot 56 in other side wall 57. Both slots 54 and 56 are the only entrance slots into interior 58 of the cover. As such, there are no vent openings located on the top of the cover.

Figure 15:
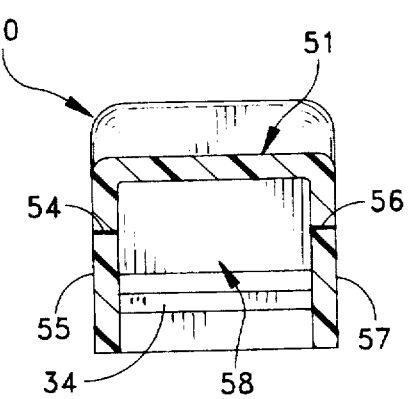
FIG. 15 is a cross-sectional view of the second alternate embodiment depicting the arched-shaped slot in its closed depressed suction applied state taken along line 15—15 of FIG. 12.

FIG. 15 shows arched-shaped slots 54 and 56 depressed closed to seal off all or most all atmospheric air from entering the interior 58. This novel configuration depicted in FIGS. 11, 12, 13, 14 and 15 shows that these slots 54 and 56 do not need to seal on any internal flange surface located on the valve body. These slots 54 and 56 can then act completely independently either in the depressed or non-depressed position independent of any internal flange surface. This means that the cover can have total flexibility in shape or contour since it does not depend upon interaction of the slots with any mating surfaces on another element such as the internal valve body. In this embodiment, the concave shape of the top wall section 51 is primarily for comfortable receipt of the user's thumb thus ensuring a better grasp rather than touch or feel sensitivity as in that embodiment illustrated in FIGS. 8–10.

It is understood that only one slot could act just as well as two slots provided that one singular slot is made larger and has the same open to atmosphere area as two smaller slots. In addition, the slots can be shaped in various configurations other than arched shaped such as rectangular in shape, oval in shape or a series of small slots in the side wall or walls. Also since it is not necessary or desirable that the top wall 51 contact the stem flange 21 or the vent opening 20 defined therein in this embodiment, it should be pointed out that the interior portions of the closure boot above the stem flange or other configured stem terminal surface form an essentially air tight plenum P such that air access to such plenum is only via the side wall vent opening or openings (slots 54).

Figure 16:
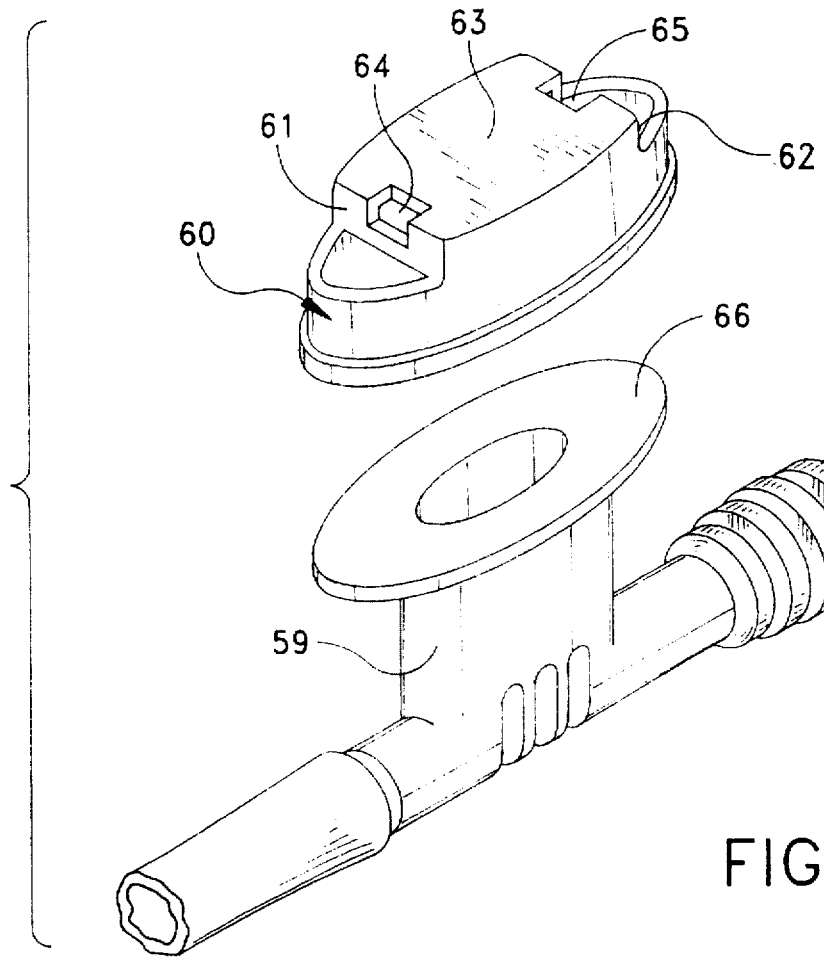
FIG. 16 is an exploded perspective view of a third alternate embodiment showing a valve body and a boot cover.

FIG. 16 depicts a third alternate embodiment showing a rigid injection molded valve body 59 similar in design to valve body 11 shown in FIG. 1. Boot cover 60 is molded in one piece of synthetic rubber and has two slightly raised side walls 61 and 62. Mounted on top of side walls 61 and 62 is diaphragm 63. Molded into side walls 61 and 62 are corresponding vent slots 64 and 65.

Figure 17:
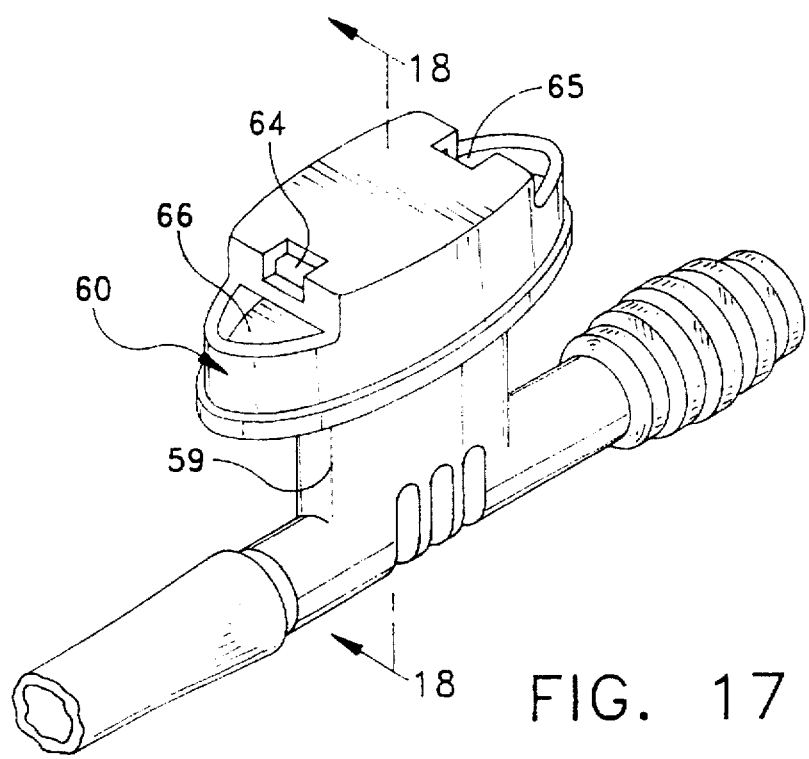
FIG. 17 is a perspective view of the embodiment of FIG. 16 with the boot cover installed on the valve body.

FIG. 17 depicts boot cover 60 mounted onto valve body stem 59 as an assembly.

Figure 18:
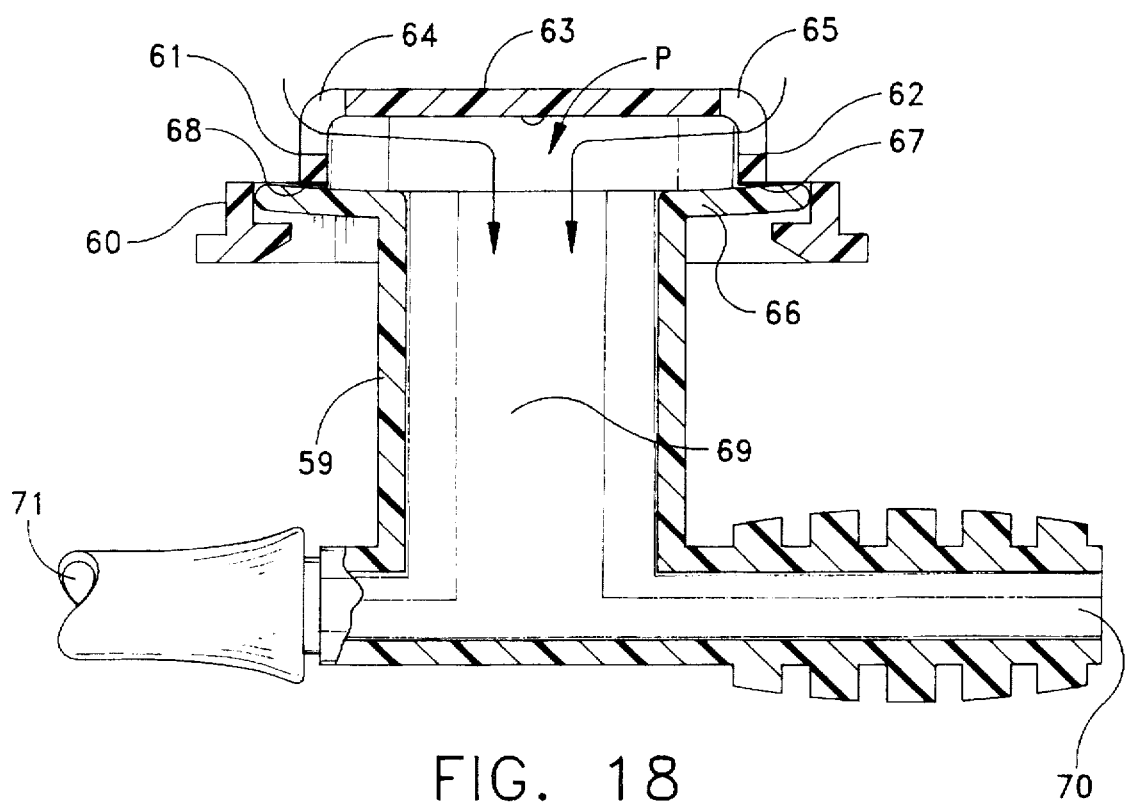
FIG. 18 is a cross-sectional view of the boot cover installed on the valve body in its normally non-suction applied open to atmosphere position taken along line 18—18 in FIG. 17.

FIG. 18 shows a cross-sectional view of boot cover 60 mounted onto valve body stem 59. Diaphragm 63 is suspended above flange 66 by supporting side walls 61 and 62 which also act as sealing surfaces 67 and 68 against flange 66 on valve body stem 59. Atmospheric air can only enter into inner passageway 69 in valve body 59 by way of side wall vent slots 64 and 65.

When suction is applied to connector 70, the suction is vented to atmosphere through side wall vent slots 64 and 65 to prevent any suction from being applied to catheter lumen 71 and the assembly is now in its normally open to atmosphere non-suction applied position.

Figure 19:
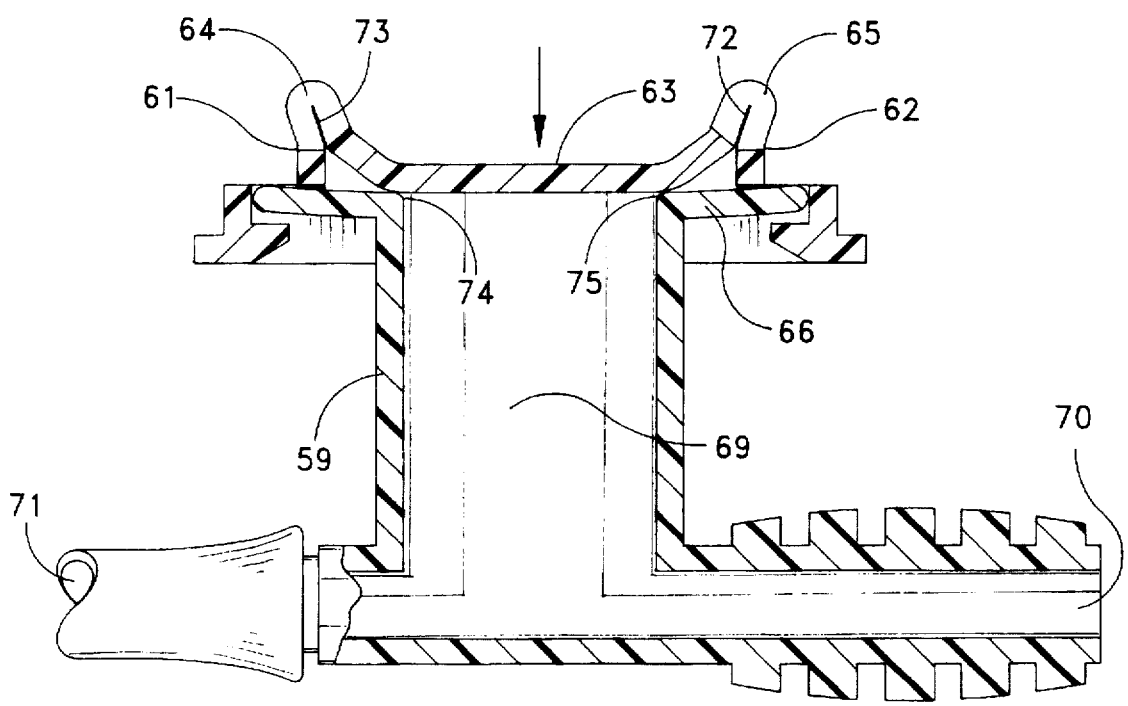
FIG. 19 is a view similar to that of FIG. 18 but with the boot cover in the closed suction applied position.

FIG. 19 depicts the same assembly in its closed suction applied position wherein diaphragm 63 is manually depressed by the user and side walls 61 and 62 flex back on themselves such that vent slots 64 and 65 move downward and inward on themselves to seal on respective sealing surfaces 72 and 73. In addition, diaphragm 63 seals on inner flange surfaces 74 and 75 to form an inner seal.

As such, the vent slots are self sealing. When suction is applied to connector 70 and diaphragm 63 is depressed, vent slots 64 and 65 self seal to close off inner passageway 69 in valve body 59 to atmosphere such that all the suction can then be applied to catheter lumen 71. In effect then, there can be two separate seals provided in this embodiment, that is, the seals brought about by the flexure of slots 64, 65, and the seal of the under surface of the closure top, that is, the diaphragm 63 against the central vent outlet defined by flange 66. These sealing actions can be either simultaneous or sequential dependent on the effects desired but normally the seal brought about by the slots occurs initially and then the seal against the central vent opening by the diaphragm occurs second and this second seal can act as a more sensitive fine tuning of the amount of suction applied to the catheter or vice-versa. In addition, a plenum P is formed above the flange as in the embodiment of FIGS. 11–15.

Figure 20:
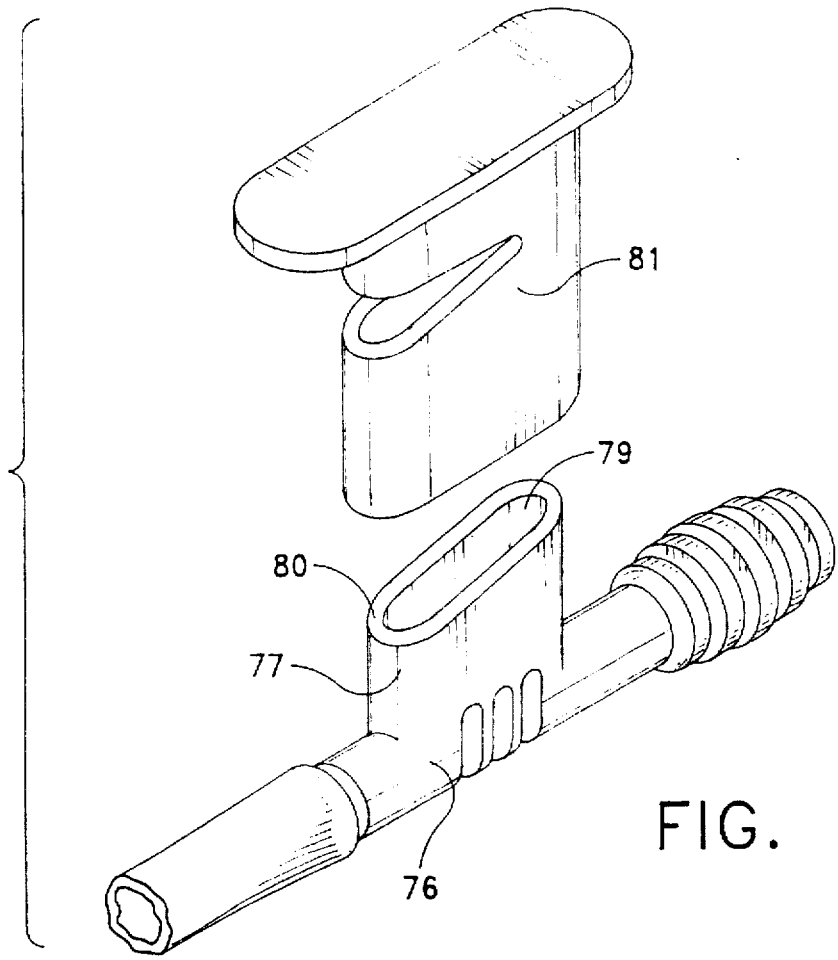
FIG. 20 is an exploded perspective view of a fourth alternate embodiment showing a valve body and a closure cap.

FIG. 20 depicts a fourth alternate embodiment wherein rigid molded valve body 76 has a narrow slimly contoured side stem 77 terminating in a flattened elliptical opening 79 with an upper outer edge 80 that is preferably formed at an acute angle, e.g., upwardly angled from left to right and longitudinally oriented as shown in the drawings.

Figure 21:
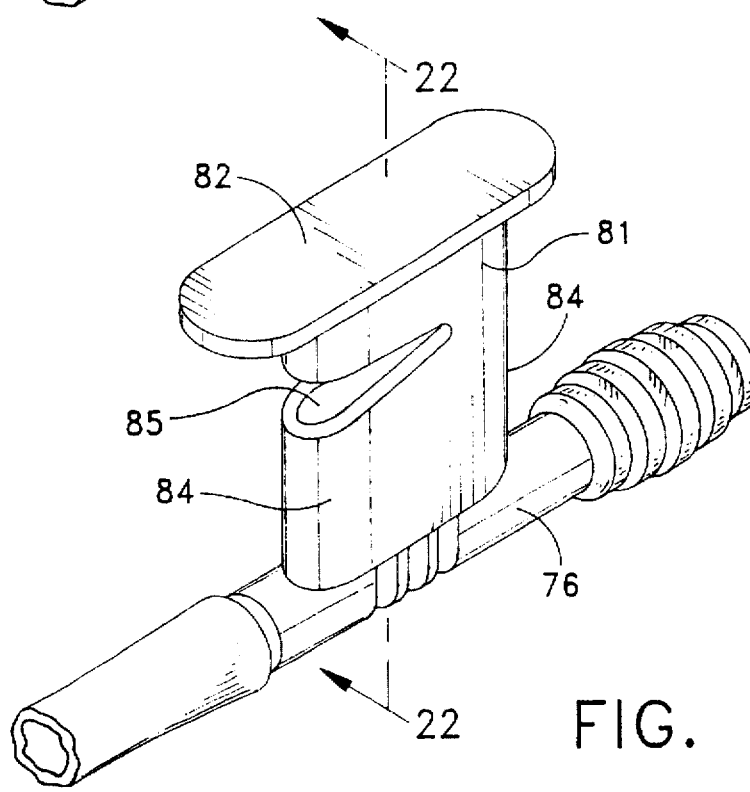
FIG. 21 is a perspective view of the embodiment of FIG. 20 with the closure cap installed on the valve body.

FIG. 21 depicts one piece resiliently molded closure cap 81 mounted onto valve body 76. Cap 81 has a contoured top 82 to conform to the thumb with side walls 84. The top 82 could alternatively be completely flat although the slight contour depicted is preferred. The top may also be provided with an outwardly extending rim portion 83 which may extend beyond the perimeter of the edge 80 and to provide adequate area for receipt of the user's thumb. Molded into side wall 84 is wedge-shaped slot 85.

Figure 22:
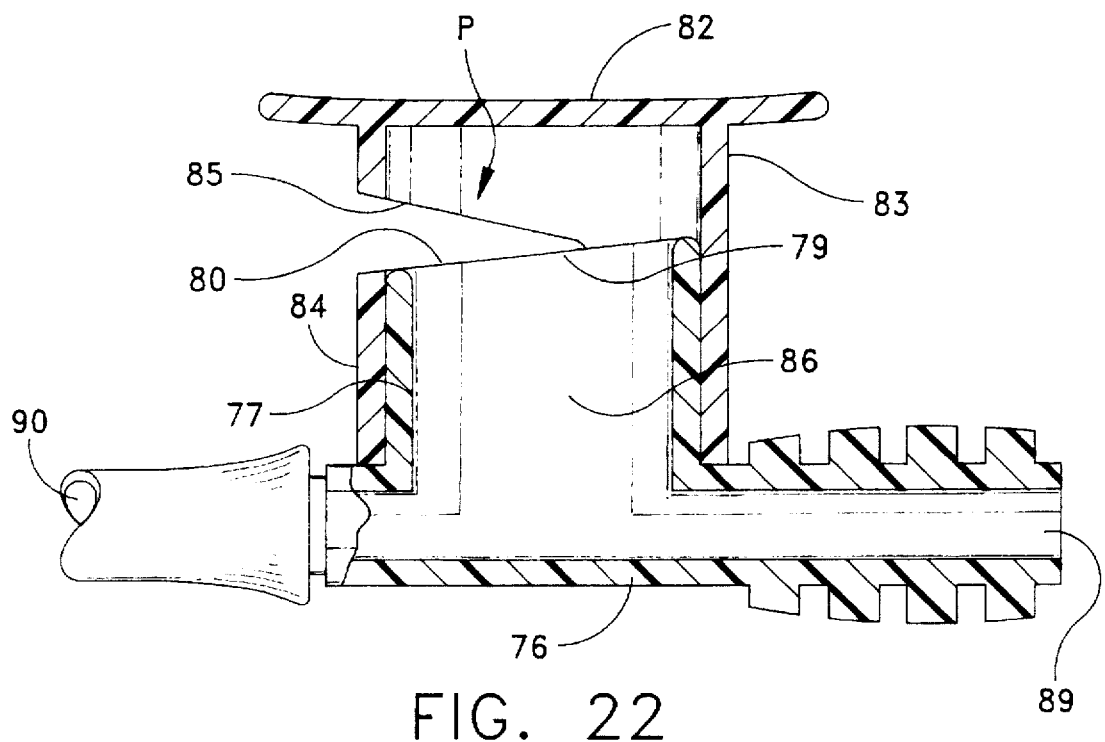
FIG. 22 is a cross-sectional view of the closure cap installed on the valve body in its normally non-suction applied open to atmosphere position taken along line 22—22 in FIG. 21.

FIG. 22 is a cross-sectional view of FIG. 21 wherein cap 81 is shown press fit onto side stem 77. Wedged-shaped slot 85 is shown in its open position wherein any suction applied to connector 89 will be vented to atmosphere through passage 86 and out wedged-shaped slot 85. An essentially air tight plenum P, as in the embodiments of FIGS. 11–15 and 16–19, is thus formed above the outer edge of the opening 79 broken only by the presence of slot 85.

Figure 23:
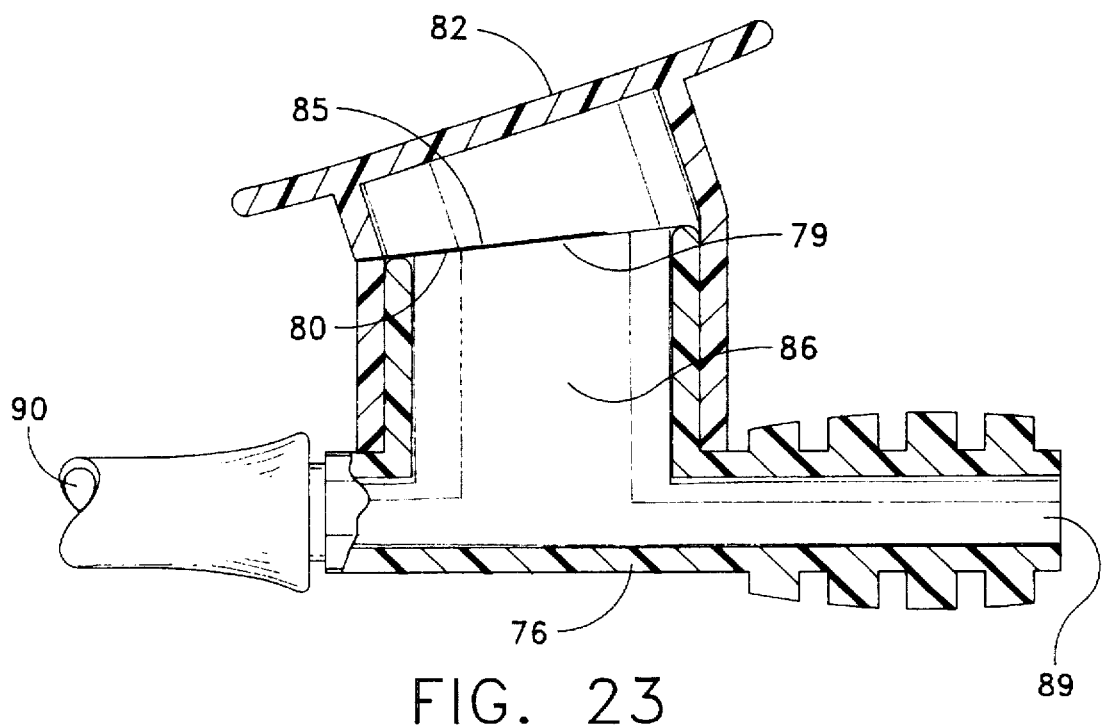
FIG. 23 is a view similar to that of FIG. 22 but with the closure cap in the closed suction applied position.

FIG. 23 shows the valve in its closed suction applied position wherein top 82 is manually depressed which moves wedged-shaped slot 85 to a sealed closed position such that slot 85 seals off on itself. The upper of the opposed surfaces which form slot 85 may also in part seal off on chamfered edge 80 of opening 79. In other words, it is possible that the slot 85 could allow some slight lateral movement to that portion of the cap 81 above the slot and having, in effect, a doubly wide surface on which the upper slot surface can sealingly contact when depressed could be desirable. Naturally to take advantage of such, in effect, double width lower surface, it is necessary to have the edge 80 and the lower surface of slot 85 positioned at the same general level and be configured at the same angular relation. In that regard, it should also be brought out that neither the stem edge 80 or the lower surface of slot 85 need be at the particular angle shown and could even be flat, that is, horizontal, although such configuration could place the top 82 at an angle when in the non-suction applied position. Also, it is not necessary for the stem to terminate at the same general level as the slot 85 as it could terminate either therebelow or could extend upwardly into the cap interior well above the slot 85, however, as the upward extent of the stem into the cap increases so does the stability of the side walls 84 which can be of importance to assure aligned closing of the slot 85, e.g., when utilizing very flexible side walls 84. Naturally, the higher the stem, in effect, extends into the cap, the greater the stability effect afforded but some caution should be exercised so that the top of the stem will not interfere with the bending of the upper cap portion necessary when the cap is moved to its slot sealing position as shown in FIG. 23. Also, the stem terminal end and terminal edge 80 need not play any role in the opening and closing of slot 85 other than provide a mount for the cap 81, e.g., when the cap is formed of material which imparts the right level of rigidity and flexibility or when no double thickness sealing surface as above described is sought. Sealing off opening 79 when suction is applied to connector 89 will seal off inner passage 86 to atmosphere such that all the suction applied will be directed to catheter lumen 90. Manual release of cover 82 will return the cap to its original open to atmosphere, non-suction applied position. The cover can be either fully or partially depressed to apply a variety of desired suction applications from continuous to intermittent to variable depending upon the degree of thumb pressure applied to the cover to either fully seal or partially seal off the slot.

The fourth embodiment depicted in FIG. 21 shows a very compact slim line suction control regulator wherein the side stem has no outwardly extending flange to add bulk to the device. Packaging of this slim line version will be much easier, faster and less costly with less packaging material on automatic sterile packaging machinery.

As can be seen, many variations in vent slots, diaphragm configurations and cover styles can be easily devised to fit whatever shaped valve flange or stem is desired. Typically, the cover or closure boot could be molded in a 70 Durometer Shore A hardness synthetic medical grade rubber material such as Monsanto Santoprene. The durometer can be varied to give any desired degree of tactile feel to the diaphragm. In addition, the regulator can be used on any medical suction instrument and should not be limited to just suction catheter use.

While certain specific structures of the invention are shown and described, it would be easy for those skilled in the art to make many and varied modifications to the parts or their assembly without departing from the spirit and scope of the underlying inventive concept. For instance, variously shaped side stems, flanges, boot covers and vent slots as well as various means for fitting the boot cover over the flange can be devised while still maintaining the basic principles of the invention.

I claim:

1. A closure adapted for a suction control regulator of the type having a body with an unobstructed suction lumen and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, said closure comprising an open ended bottom, a connecting side wall and an imperforate top wall, said closure operationally connected to the stem so that said closure is adapted to float with respect to the stem between a normally open non-suction applied position wherein said top wall is suspended above said side stem upper end terminal surface to an alternate closed suction applied position, said top wall being adapted to be superimposed over and to completely cover the stem vent opening, said closure side wall extending downwardly from said top wall and including at least one vent opening therethrough and in turn adapted for communication with the stem vent opening, said top wall being manually downwardly depressible so as to close off said side wall vent opening from communication with the stem vent opening thereby moving the regulator to its alternate closed suction applied position.

2. The closure of claim 1, wherein said both closure top wall and said stem terminal surface include lateral and longitudinal extending portions and wherein said top wall extends beyond the stem vent opening in the side stem terminal surface along each of said lateral and longitudinal extending portions.

3. A closure adapted for a suction control regulator of the type having a body with an unobstructed suction lumen and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, said closure comprising an open ended bottom, a connecting side wall and a top wall and adapted for operational connection to the stem between a normally open non-suction applied position to an alternate closed suction applied position, said top wall being adapted to be superimposed over and to completely cover the stem vent opening, said closure side wall extending downwardly from said top wall and including at least one vent opening therethrough and in turn adapted for communication with the stem vent opening, said top wall being manually downwardly depressible so as to close off said side wall vent opening from communication with the stem vent opening thereby moving the regulator to its alternate closed suction applied position, said stem terminal surface including lateral and longitudinal extending portions and wherein said top wall extends beyond the stem vent opening in the stem terminal surface along each of said lateral and longitudinal extending portions, wherein the closure is of a longitudinal extent greater than that of its lateral extent so as to present an overall generally flat sided, oval, planar configuration and defining longitudinally opposed terminal ends with said side wall vent opening positioned proximal one of said terminal ends.

4. The closure of claim 3, wherein there is a pair of side wall vent openings positioned proximal each of said terminal ends and adjacent said top wall at logitudinally opposed ends thereof.

5. The closure of claim 1 wherein the suction control regulator side stem upper end terminal surface is in the form of a thumb conformable flange through which the stem suction vent opening extends and wherein said top wall is adapted to contact the flange to seal off the stem suction vent opening in the closed suction applied position.

6. The closure of claim 5, the flange and said closure both of generally flat-sided, oval configuration and wherein there is a pair of side wall vent openings positioned adjacent said top wall.

7. A closure adapted for a suction control regulator of the type having a body with an unobstructed suction lumen and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, said closure comprising an open ended bottom, a connecting side wall and a top wall and adapted for operational connection to the stem between a normally open non-suction applied position to an alternate closed suction applied position, said top wall being adapted to be superimposed over and to completely cover the stem vent opening, said closure side wall extending downwardly from said top wall and including at least one vent opening therethrough and in turn adapted for communication with the stem vent opening, said top wall being manually downwardly depressible so as to close off said side wall vent opening from communication with the stem vent opening thereby moving the regulator to its alternate closed suction applied position, and wherein the suction control regulator side stem upper end terminal surface is in the form of a thumb conformable flange through which the stem suction vent opening extends and wherein said top wall is adapted to contact the flange to seal off the stem suction vent opening in the closed suction applied position, the flange and said closure both of generally flat-sided, oval configuration and wherein there is a pair of side wall vent openings positioned adjacent said top wall, and wherein the side wall vent openings have opposed upper and lower side wall vent opening defining surfaces, said opening defining surfaces movable from the open to atmosphere position wherein said surfaces are vertically spaced from each other to the closed to atmosphere position wherein at least portions of said opening defining surfaces contact each other so as to close said side wall vent openings.

8. The closure of claim 1, said closure being a flexible boot adapted to freely fit over the regulator body stem.

9. A closure adapted for a suction control regulator of the type having a body with an unobstructed suction lumen and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, said closure comprising an open ended bottom, a connecting side wall and a top wall and adapted for operational connection to the stem between a normally open non-suction applied position to an alternate closed suction applied position, said top wall being adapted to be superimposed over and to completely cover the stem vent opening, said closure side wall extending downwardly from said top wall and including at least one vent opening therethrough and in turn adapted for communication with the stem vent opening, said top wall being manually downwardly depressible so as to close off said side wall vent opening from communication with the stem vent opening thereby moving the regulator to its alternate closed suction applied position, and wherein the suction control regulator side stem upper end terminal surface is in the form of a thumb conformable flange through which the stem suction vent opening extends and wherein said top wall is adapted to contact the flange to seal off the stem suction vent opening in the closed suction applied position, the flange and said closure both of generally flat-sided, oval configuration and wherein there is a pair of side wall vent openings positioned adjacent said top wall, and each of said side wall openings comprising a plurality of secondary side wall openings.

10. The closure of claim 1, said closure with the exception of said side wall vent opening is adapted to form an essentially air tight plenum above the stem vent.

11. A closure adapted for a suction control regulator of the type having a body with an unobstructed suction lumen and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, said closure comprising an open ended bottom, a connecting side wall and a top wall and adapted for operational connection to the stem between a normally open non-suction applied position to an alternate closed suction applied position, said top wall being adapted to be superimposed over and to completely cover the stem vent opening, said closure side wall extending downwardly from said top wall and including at least one vent opening therethrough and in turn adapted for communication with the stem vent opening, such that said closure with the exception of said side wall vent opening is adapted to form an essentially air tight plenum above the stem vent, said top wall being manually downwardly depressible so as to close off and seal said side wall vent opening from communication with the stem vent opening thereby moving the regulator to its alternate closed suction applied position, wherein said at least one side wall vent opening has opposed upper and lower side wall vent opening defining surfaces, said opening defining surfaces movable from the open to atmosphere position wherein said surfaces are vertically spaced from each other to the closed to atmosphere position wherein at least portions of said opening defining surfaces contact each other so as to close said side wall vent openings.

12. The closure of claim 11 wherein the suction control catheter regulator side stem upper end terminal surface is in the form of a thumb conformable flange through which the stem suction vent opening extends, there being a pair of side wall vent openings disposed longitudinally spaced from each other at opposed longitudinal ends of the closure and wherein said contact between said side wall opening defining surfaces occurs above the flange surface and longitudinally offset from the stem vent opening.

13. The closure of claim 11, said side wall vent opening being an arched shaped slot formed in said side wall.

14. The closure of claim 13, said closure of an overall longitudinally elongated configuration with pairs of both laterally and longitudinally extending side wall portions connected to each other and opposed to each other, said longitudinally extending side wall portions each having an arched shape slot formed therein.

15. The closure of claim 11, said at least one side wall vent opening being a generally V-shaped slot having a pair of legs connected at one end thereof and open at the other end thereof with said legs oriented longitudinally and with said open end positioned at an outside side wall surface and extending into the side wall therefrom and wherein said slot is adapted to close upon itself in the closed suction applied position.

16. A suction control catheter assembly comprising a suction control regulator and a closure therefor, said suction control regulator having a body in turn having front and rear ends with an unobstructed suction lumen passing therethrough and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, a suction tube attached to the front end of the body and the rear end of the body adapted for connection to a source of suction, said closure having an open ended bottom, a connecting side wall and an imperforate top wall, said closure operationally connected to the stem so that said closure is adapted to float with respect to said stem between a normally open non-suction applied position to an alternate closed suction applied position, wherein said top wall is suspended above said side stem upper end terminal surface, said top wall being superimposed over and completely covering the stem vent opening, said closure side wall extending downwardly from said top wall and including at least one vent opening therethrough and in communication with the stem vent opening, said top wall being manually downwardly depressible so as to close off said side wall vent opening from communication with said stem vent opening thereby moving the regulator to its alternate closed suction applied position.

17. The assembly of claim 16, said side stem terminal surface being an elongated flange, said closure top wall downwardly depressible into contact with said flange so as to seal off said stem suction vent opening.

18. The assembly of claim 16, said closure with the exception of said side wall vent opening forming an essentially air tight plenum above said stem vent opening and said movement of said top wall to the closed suction applied position further sealing said side wall vent opening.

19. The assembly of claim 18, wherein said at least one side wall vent opening has opposed upper and lower side wall vent opening defining surfaces, said opening defining surfaces movable from the open to atmosphere position wherein said surfaces are vertically spaced from each other to the closed to atmosphere position wherein at least portions of said opening defining surfaces contact each other so as to close said at least one side wall vent opening.

20. A suction control catheter assembly comprising a suction control regulator and a closure therefor, said suction control regulator having a body in turn having front and rear ends with an unobstructed suction lumen passing therethrough and a side stem portion which extends outwardly therefrom at an intermediate point of the suction lumen and wherein the side stem terminates in an upper end having a terminal surface in part defining a stem suction vent opening in turn communicating with a passage in the stem which serves to connect the stem vent opening with the lumen, a suction tube attached to the front end of the body and the rear end of the body adapted for connection to a source of suction, said closure having an open ended bottom, a connecting side wall and a top wall and adapted for operational connection to said stem between a normally open non-suction applied position to an alternate closed suction applied position, said top wall being superimposed over and completely covering the stem vent opening, said closure side wall extending downwardly from said top wall and including at least one vent opening therethrough and in communication with the stem vent opening, said top wall being manually downwardly depressible so as to close off said side wall vent opening from communication with said stem vent opening thereby moving the regulator to its alternate closed suction applied position, said closure including a bottom peripheral surface which defines said open bottom, said bottom peripheral surface downwardly spaced from said side stem upper end and contacting upper portions of said regulator body.

21. The assembly of claim 16, said at least one side wall vent opening being a generally V-shaped slot having a pair of legs connected at one end thereof and open at the other end thereof with said legs oriented longitudinally and with said open end positioned at an outside side wall surface and extending into the side wall therefrom and wherein said slot is adapted to close upon itself in the closed suction applied position.

22. The assembly of claim 21, wherein said side stem portion is of an overall elliptical configuration longitudinally extending in line with the longitudinal extent of said regulator body and wherein said side stem terminal surface upwardly slants from that side proximal to said slot open end.

23. The assembly of claim 16, wherein said closure top wall includes lateral and longitudinal extending portions and wherein said top wall extends beyond the stem vent opening in the stem terminal surface along each of said lateral and longitudinal extending portions and wherein the closure is of a longitudinal extent greater than that of its lateral extent so as to present an overall generally flat sided, oval, planar configuration and defining longitudinally opposed terminal ends with said side wall vent opening positioned proximal one of said terminal ends.

24. The assembly of claim 16, wherein said at least one side wall vent opening has opposed upper and lower side wall vent opening defining surfaces, said opening defining surfaces movable from the open to atmosphere position wherein said surfaces are vertically spaced from each other to the closed to atmosphere position wherein at least portions of said opening defining surfaces contact each other so as to close said side wall vent openings.

25. The assembly of claim 16 wherein the suction control catheter regulator side stem upper end terminal surface is in the form of a thumb conformable flange through which the stem suction vent opening extends, there being a pair of side wall vent openings disposed longitudinally spaced from each other at opposed longitudinal ends of the closure and wherein said contact between said side wall opening defining surfaces occurs above the flange surface and longitudinally offset from the stem vent opening.

26. The assembly of claim 16, wherein said side wall vent opening being an arched shaped slot formed in said side wall.

27. The assembly of claim 16, said closure of an overall longitudinally elongated configuration with pairs of both laterally and longitudinally extending side wall portions connected to each other and opposed to each other, said longitudinally extending side wall portions each having an arched shape slot formed therein.

28. The assembly of claim 17, wherein said side wall includes holding means inwardly extending from said side wall to a position inwardly beneath said flange for holding said closure on said side stem.

29. The assembly of claim 28, said closure including a bottom peripheral surface which defines said open bottom, said bottom peripheral surface downwardly spaced from said side stem upper end and contacting upper portions of said regulator body.

30. The assembly of claim 16, said closure being a flexible boot adapted to freely fit over the regulator body stem.

31. The assembly of claim 16, wherein said stem terminal surface includes lateral and longitudinal extending portions and wherein said top wall extends beyond the stem vent opening in the side stem terminal surface along each of said lateral and longitudinal extending portions.

32. The assembly of claim 20, wherein said closure being a flexible boot adapted to freely fit over the regulator body stem.

33. The assembly of claim 20, wherein said side stem terminal surface is an elongated flange and said side wall includes holding means inwardly extending from said side wall to a position inwardly beneath said flange for holding said closure on said side stem.

* * * * *